(12) United States Patent
Puusaari et al.

(10) Patent No.: US 7,508,906 B2
(45) Date of Patent: Mar. 24, 2009

(54) FILTER FOR X-RAY RADIATION, AND AN ARRANGEMENT FOR USING FILTERED X-RAY RADIATION FOR EXCITATION

(75) Inventors: Erikki Puusaari, Espoo (FI); Andy Ellis, Sutton Courtenay (GB)

(73) Assignee: Oxford Instruments Analytical Oy, Espoo (FI)

( * ) Notice: Subject to any disclaimer, the term of this patent is extended or adjusted under 35 U.S.C. 154(b) by 55 days.

(21) Appl. No.: 11/789,854

(22) Filed: Apr. 26, 2007

(65) Prior Publication Data

US 2008/0267348 A1   Oct. 30, 2008

(51) Int. Cl.
*G01N 23/223* (2006.01)
(52) U.S. Cl. ........................................ 378/44; 378/157
(58) Field of Classification Search ............. 378/44–50, 378/156–159
See application file for complete search history.

(56) References Cited

U.S. PATENT DOCUMENTS

2004/0136500 A1 *  7/2004  Amemiya et al. ........... 378/157

* cited by examiner

*Primary Examiner*—Courtney Thomas
(74) *Attorney, Agent, or Firm*—Wood, Phillips, Katz, Clark & Mortimer

(57) ABSTRACT

An X-ray fluorescence measurement device comprises an X-ray source and a sample window for allowing X-rays from the X-ray source reach a sample. A filter arrangement between the X-ray source and the sample window includes a first filter layer comprising a first filtering element and a second filter layer including a second filtering element. The atomic number of the second filtering element is greater than the atomic number of the first filtering element. The first filter layer is between the X-ray source and the second filter layer.

15 Claims, 2 Drawing Sheets

Fig. 3a
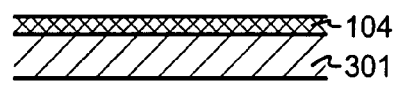
Fig. 3b
Fig. 3c
Fig. 3d
Fig. 3e
Fig. 3f
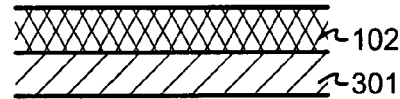
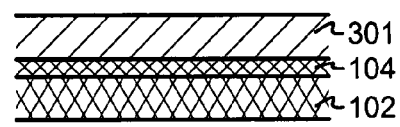
Fig. 3g
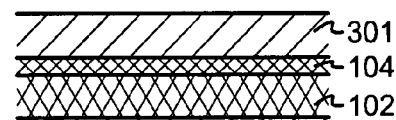
Fig. 3h
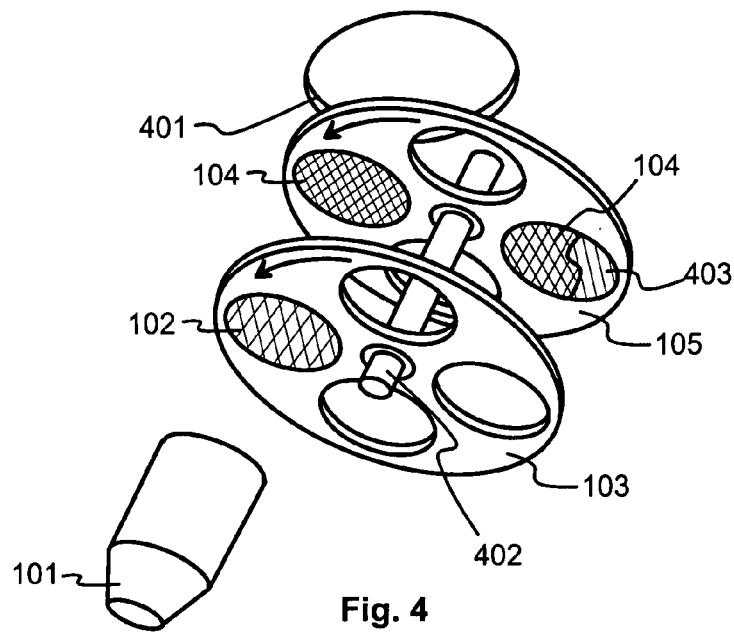
Fig. 4

US 7,508,906 B2

FILTER FOR X-RAY RADIATION, AND AN ARRANGEMENT FOR USING FILTERED X-RAY RADIATION FOR EXCITATION

TECHNICAL FIELD

The invention concerns in general the technology of X-ray fluorescence analysis. Especially the invention concerns the problem of suitably shaping the spectrum of the incident radiation used for excitation.

BACKGROUND OF THE INVENTION

X-ray fluorescence (XRF) analysis is a good way of detecting the presence of heavy metals in samples made of e.g. plastic or other matrix material. For example, enforcing the RoHS (Restriction of Hazardous Substances) directive of the European Union requires capability of measuring, how much a sample contains lead, cadmium, mercury, hexavalent chromium, and polybrominated biphenyl (PBB) and polybrominated diphenyl ether (PBDE) flame retardants, to which purpose XRF is well suited. The two last-mentioned substances are conveniently detected by measuring the amount of bromine in the sample. Other standards exist also that require good XRF detection capabilities.

Detecting heavy elements in an XRF measurement requires the incident X-ray radiation that is used as excitation to be relatively energetic. The natural output spectrum of a typical 40 kV X-ray tube does not have the best possible shape, for a number of reasons. As an exemplary material to be detected we will consider cadmium (Cd). If the anode material of the X-ray tube is rhodium (Rh), only the continuous high-energy bremsstrahlung part of the incident radiation is useful, because the K-lines of Rh (20.2 keV and 22.7 keV) are below the K-shell absorption edge (26.7 keV) of Cd. Some line structure in the excitation spectrum would be needed to perform the so-called matrix correction, which means deconvolving the detected fluorescence spectrum into Compton scattered and coherently scattered parts and analysing their relative intensities. If the anode material is heavier, like tungsten (W), the proportional intensity of the useful excitation radiation is higher and the characteristic L-line peaks of W would basically be available for matrix correction. However, with a W anode the Compton scatter peaks are relatively close to the coherent scatter peaks, which makes spectrum deconvolution difficult. Also, the L-lines of W (8.39 keV and 9.67 keV) overlap with spectral lines of some interesting materials to be detected, which means that they must be filtered out, again leaving the excitation spectrum without the required structure.

Other known anode materials for so-called high-Z X-ray tubes include but are not limited to rhenium (Re), platinum (Pt), and gold (Au).

It is known from prior art to shape the spectrum of incident X-ray radiation by using a filter between the X-ray source and the sample. A molybdenum (Mo) filter in front of a 40 kV X-ray tube with a tungsten anode would serve many purposes. It would effectively filter out the L-line peaks of W, and give rise to characteristic incident radiation peaks of Mo at 17.5 keV (K-alpha), 19.6 keV (K-beta), 2.29 keV (L-alpha), and 2.39 keV (L-beta). The energies are high enough and far enough apart for good separation of Compton and coherent scattering peaks, and do not overlap with those spectral lines that are important for analysing the substances mentioned in the RoHS directive. However, such a Mo filter also absorbs significant quantities of the bremsstrahlung above 26.7 keV, which would be needed for Cd excitation. The thickness of the Mo filter is an awkward tradeoff: the thinner the filter, the less there occurs unwanted absorption at energies above 26.7 keV, but the lower is also the intensity of the characteristic Mo peaks, which would be needed for the matrix correction, and the weaker is the desired effect of filtering out the unwanted spectral lines of the anode material.

SUMMARY OF THE INVENTION

An objective of the present invention is to present a method and an apparatus for producing a beam of incident X-ray radiation that has suitable spectral characteristics for use in analysing heavy elements such as cadmium. Another objective of the invention is to facilitate flexible changes in the shaping of the spectrum of such incident X-ray radiation. Yet another objective of the invention is to implement the shaping of the spectrum of such incident X-ray radiation with low production costs.

The objectives of the invention are achieved with a filter arrangement in which a first filter layer, which comprises a lighter filtering element, is followed by a second filter layers which comprises a heavier filtering element. At least one of the filter layers may be movably supported between the X-ray source and the sample.

A filter arrangement for X-ray radiation according to the invention is characterized in that it comprises:
  a first filter layer comprising a first filtering element, which has an atomic number, and
  a second filter layer comprising a second filtering element, which has an atomic number that is greater than the atomic number of the first filtering element;
  wherein said first filter layer and said second filter layer are adapted to be supported between an X-ray source and a sample to be subjected to X-ray fluorescence analysis, and said first filter layer is adapted to be supported between said X-ray source and said second filter layer.

An X-ray fluorescence measurement device according to the invention is characterized in that it comprises:
  an X-ray source,
  a sample window for allowing X-rays from said X-ray source reach a sample to be subjected to X-ray fluorescence analysis, and
  a filter arrangement between said X-ray source and said sample window;
  wherein said filter arrangement comprises a first filter layer comprising a first filtering element, which has an atomic number, and a second filter layer comprising a second filtering element, which has an atomic number that is greater than the atomic number of the first filtering element, and said first filter layer is between said X-ray source and said second filter layer.

An element being lighter than another element means that its atomic number is less, and correspondingly an element being heavier than another element means that its atomic number is greater A lighter element, such as nickel (Ni) or copper (Cu), will typically have a larger absorption cross-section for X-rays at lower energies and smaller at higher energies. This means that a layer of such a lighter element in front of an X-ray source will filter out proportionally more of the low-energy part of the radiation that comes out of the X-ray source.

Simultaneously, the atoms of the lighter element will experience excitation and emit characteristic X-rays at K- and L-line energies. If a layer of a suitably selected heavier element, such as rhodium (Rh) or palladium (Pd), is placed between the lighter element layer and a sample, the same effect will be repeated with different energies: some overall absorption will occur in the subsequent layer, but most of all it will absorb the characteristic peaks of the lighter element, and give rise to new characteristic peaks at the L- and possibly K-line energies of the heavier material.

It has been found that it is possible to select the materials and layer thicknesses in a suitable manner, so that the excitation radiation that eventually hits the sample contains a significant amount of the high-energy bremsstrahlung combined with the advantageously located characteristic peaks of the heavier filtering element. One exemplary combination is a 20 micrometers thick Ni or Cu layer followed by a 3.5 micrometers thick Rh or Pd layer. The layers may be mechanically separate from each other, or they may be combined into a single mechanical entity. A support layer or a number of support layers made of material essentially transparent to X-rays may be used to mechanically reinforce the structure. At least one of the layers may be placed into a movable filter changer, with which it can be moved in and out from between the X-ray source and the sample.

The exemplary embodiments of the invention presented in this patent application are not to be interpreted to pose limitations to the applicability of the appended claims. The verb "to comprise" is used in this patent application as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIGS. 3a to 3h illustrate various two-layer filter arrangements, and

FIG. 4 illustrates certain parts of an X-ray fluorescence measurement device.

DETAILED DESCRIPTION OF THE INVENTION

Figure 1:
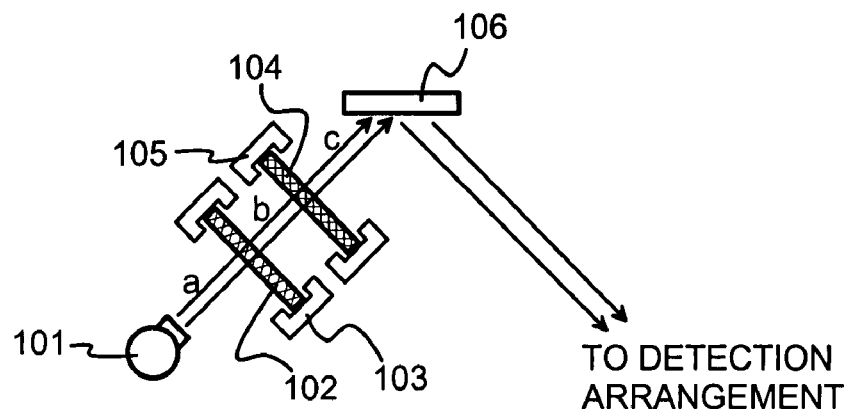
FIG. 1 illustrates a principle of using two different filter layers between an X-ray source and a sample.
Figure 2A:
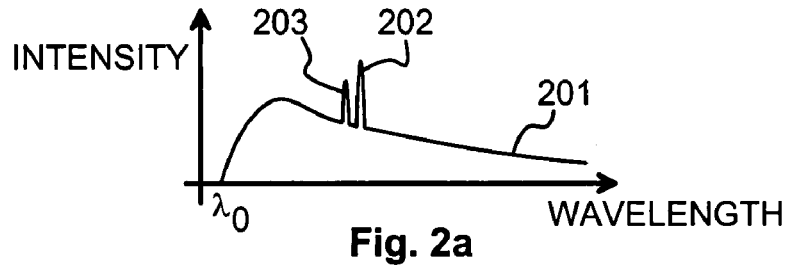
FIG. 2a illustrates a spectrum of incident X-ray radiation.

FIG. 1 illustrates schematically certain parts of an X-ray fluorescence analyzer device. An X-ray tube 101, which here is schematically shown as being of the side window type but which could also be of the end window type, acts as the source of incident X-rays. FIG. 2a illustrates schematically the intensity of the incident X-rays at location a in FIG. 1 as a function of wavelength. The continuous curve 201 illustrates the bremsstrahlung part of the incident X-rays. The shortest wavelength limit $\lambda_0$ comes from the acceleration voltage of the X-ray tube 101, and any characteristic peaks (of which exemplary peaks 202 and 203 are shown in FIG. 2a) correspond to the electron shell structure of the anode material used in the X-ray tube 101. Here we assume that the anode material is tungsten, and the peaks 202 and 203 occur at 1.48 and 1.28 ångströms corresponding to the L-line energies 8.39 keV and 9.67 keV of tungsten respectively.

In the following we use the expression "filter layer" to mean an essentially planar, sheet-like piece of material that can be deliberately placed on the path of X-rays in the purpose of affecting the spectrum of the X-ray radiation. We use the expression "filtering element" to mean an element that is present in or constitutes the substance of a filter layer, and that has been selected in the purpose of using the characteristic features of that element for accomplishing the desired filtering effect.

Figure 2B:
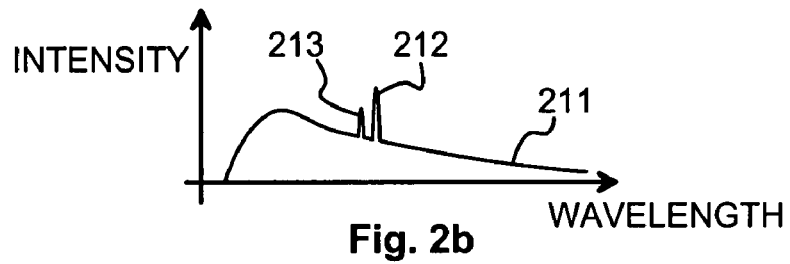
FIG. 2b illustrates a spectrum of X-ray radiation filtered once.

The incident X-rays are directed through a first filter layer 102 that comprises a first filtering element. The effect of the first filtering element is to absorb some of the incident X-rays and to produce fluorescent radiation at the characteristic wavelengths of the first filtering element. FIG. 2b illustrates schematically the intensity of X-rays at location b in FIG. 1 as a function of wavelength. The bremstrahlung curve 211 is somewhat lower than in FIG. 2a due to overall attenuation in the first filter layer, and instead of the peaks of FIG. 2a we see characteristic peaks corresponding to the electron shell structure of the first filtering element. Assuming that the first filtering element is nickel, the peaks 212 and 213 occur at 1.66 and 1.50 ångströms corresponding to the K-line energies 7.48 keV and 8.26 keV of nickel respectively. Schematically shown in FIG. 1 is also a first holder 103 that supports mechanically the first filter layer 102.

Using nickel as the first filtering element is advantageous especially if the anode material in the X-ray tube is tungsten. With X-ray tubes that have rhenium, platinum or gold as anode material, a more advantageous first filtering element is copper. If the first filtering element would be copper, FIG. 2b would exhibit characteristic peaks at 1.54 and 1.39 ångströms corresponding to the K-line energies of 8.05 keV and 8.90 keV of copper respectively.

Figure 2C:
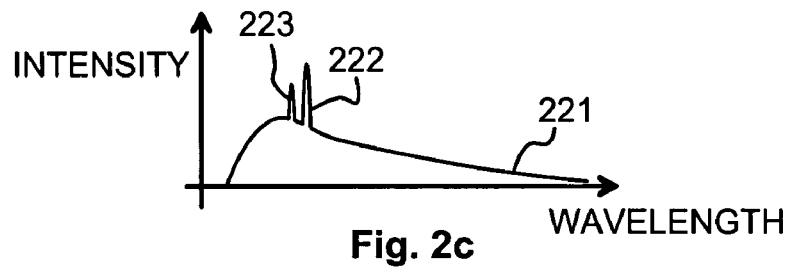
FIG. 2c illustrates a spectrum of X-ray radiation filtered twice.

The X-rays that passed the first filter layer 102, as well as that part of the characteristic radiation generated in the first filtering element that is directed to the appropriate direction, are directed through a second filter layer 104 that comprises a second filtering element. The effect of the second filtering element is again to absorb some of X-rays hitting it and to produce fluorescent radiation at the characteristic wavelengths of the second filtering element. FIG. 2c illustrates schematically the intensity of X-rays at location c in FIG. 1 as a function of wavelength. The bremstrahlung curve 221 is again somewhat lower than in FIGS. 2a and 2b due to overall attenuation in the second filter layer, and instead of the previous peaks we see characteristic peaks corresponding to the electron shell structure of the second filtering element. Assuming that the second filtering element is rhodium, the peaks 222 and 223 occur at 0.61 and 0.55 ångströms corresponding to the K-line energies 20.2 keV and 22.7 keV of rhodium respectively. Also the L-lines of rhodium would be visible, if the graphical illustration of FIG. 2c continued more to the right. If the second filtering element is palladium, the peaks 222 and 223 occur at 0.59 and 0.52 ångströms corresponding to the K-line energies 21.2 keV and 23.8 keV of palladium respectively.

Schematically shown in FIG. 1 is also a second holder 105 that supports mechanically the second filter layer 104. Together the first filter layer 102 and the second filter layer 104 constitute a filter arrangement.

FIGS. 3a to 3h illustrate some possible principles of constructing a two-layer filter arrangement. In FIG. 3a the first filter layer 102 and the second filter layer 104 are together and constitute a single mechanical entity. This possibility is advantageous in cases where at least one of the layers would be mechanically too weak to be reliably used alone, but a combination of the layers has the required mechanical strength. FIG. 3b illustrates a possibility in which the first filter layer 102 is a standalone layer but the second filter layer 104 has a support layer 301 attached to it. The support layer 301 is preferably made of some material that is essentially transparent to X-rays, like beryllium, polyimide or the like.

FIG. 3c illustrates a case in which the mechanical strength of both the first 102 and second 104 filter layers is sufficient so that they can both be used as such, without attaching them to each other or to any support layers. In FIG. 3d there is a support layer 301, and the first 102 and second 104 filter layers are attached to opposite surfaces of the support layer 301. FIG. 3e illustrates a case in which there is a first support layer 301 to support the first filter layer 102, and a second support layer 302 to support the second filter layer 104. In this case as well as in that of FIG. 3b it is immaterial, whether in the propagation direction of the X-rays (which in FIGS. 3a to 3h is from bottom to top) a support layer comes first and the filter layer attached to it thereafter, or vice versa.

FIG. 3f illustrates a combined structure in which a support layer 301 has on one of its surfaces a sandwiched structure of the first 102 and second 104 filter layers. In FIG. 3g the support layer 301 is on the other side of the stack of the first 102 and second 104 filter layers. In FIG. 3h the stack of the first 102 and second 104 filter layers is sandwiched between a first support layer 301 and a second support layer 302. The presentation of various structures in FIGS. 3a to 3h is not meant to be exhaustive, and the illustrated layer thicknesses are schematic only and not to scale. In place of any solid sheet made of a filtering element it is also possible to use various alloys, mixtures and composite structures, in which one or more filtering elements are mixed with each other and/or with some matrix material transparent to X-rays.

Regardless of the structure of the filter layers, it is typically advantageous to attach the filter layers and/or support layers to a support frame along their edges. A support frame makes it easier to handle the filters, for example to attach a filter to a holder in an X-ray measurement device.

Some consideration should be given to the selection of filtering elements and the thicknesses of the filter layers (or, in the case of alloyed filtering elements or filtering element particles diffusely located within a matrix material: effective thicknesses, meaning the thickness of a corresponding solid layer of that filtering element). The overall aim is to achieve a spectrum of the X-ray radiation impinging on the sample, which would have a large amount of bremsstrahlung more energetic than 26.7 keV and some characteristic peaks that do not overlap with characteristic peaks of sample materials to be measured. We assume that the anode material of the X-ray tube is one the characteristic peaks of which will overlap with those of some interesting sample materials. Thus the characteristic peaks of the anode material should be filtered away, preferably in the first filter layer already. A suitable first filtering element for filtering away the characteristic peaks of tungsten is nickel. A suitable first filtering element for filtering away the characteristic peaks of rhenium, platinum or gold is copper. Other choices for the first filtering element, especially for use with other anode materials, may be found by experimenting and/or simulation. If the acceleration voltage of the X-ray tube is 40 kV and tube current is in the order of 10 microamperes, the gross input power of the X-ray tube is in the order of 0.4 W. With these values a suitable thickness for the nickel or copper layer is around 20 micrometers, or between 15 and 25 micrometers.

The second filtering element has the dual purpose of filtering away the characteristic peaks of the first filtering element (and the remaining parts of the characteristic peaks of the anode material, if any), and generating some new characteristic peaks for use in the matrix correction calculations. With tungsten, rhenium, platinum or gold as anode material and nickel or copper as the first filtering element, suitable second filtering elements are rhodium and palladium. If the performance values of the X-ray tube are equal to those mentioned above (acceleration voltage about 40 kV, tube current 10 microamperes, gross input power in the order of 0.4 W, and the thickness of the nickel or copper layer is in the order of 20 micrometers, a minimum thickness for the rhodium or palladium layer is around 3.5 micrometers. In a two-layer filter arrangement a practical maximum thickness of the rhodium or palladium layer is around 50 micrometers.

The second filtering layer may be even relatively thick, in the order of 100 micrometers, if the purpose is to completely remove all interfering peaks of the other materials that could overlap with the spectral lines of cadmium in the sample. A thick second filtering layer attenuates also significantly the desired hard-end bremsstrahlung. To some extent this could be compensated for e.g. by increasing the tube current. However, a very thick "second" filtering layer soon means that a no separate "first" filtering layer is needed at all, because the thick "second" filtering layer performs all filtering that the "first" filtering layer would perform. Since there is also the mentioned problem of losing high-energy bremsstrahlung intensity, the two-layer filter arrangement is considered to be more advantageous.

FIG. 4 illustrates schematically the use of a filter changer in an XRF measurement device to selectively take into use first and second filter layers of the kinds described above. The XRF measurement device comprises an X-ray tube 101 and a sample window 401, which is meant to be placed against or towards a sample to be measured. In the space between the X-ray tube 101 and the sample window 401 the XRF measurement device comprises at least one filter changer. The device illustrated in FIG. 4 has two consecutive filter changers, each of which comprises a rotationally mounted holder. The first holder 103 is a circular plate rotationally mounted on an axis 402 and having a number of openings through it. The first filter layer 102 is adapted to cover one of said openings in the first holder 103. The second holder 105 is also a circular plate rotationally mounted on the axis 402. Also the second holder 105 defines a number of openings through it. The second filter layer 104 is adapted to cover one of said openings in the second holder 105.

The filter arrangement may comprise other filter layers than those mentioned so far. As an example, one opening of the second holder 105 comprises a two-layer filter. The first of these (in the propagation direction of the X-rays) is the similar second filter layer 104 as above; it is shown schematically as partly cut through. The other layer is a third filter layer 403. For example, one may use a relatively thick (like 200 micrometers) aluminium or other light element layer as the third filter layer 403. Aluminium will effectively filter out any remaining spectral lines of nickel or copper, without essentially attenuating the hard-end bremsstrahlung at energies above 27 keV. Since it will have the same effect regardless of at which position between the first filter layer and the sample it is, the third filter layer 403 could be located also between the first and second filter layers (so that the order of the layers 104 and 403 in this opening would be the opposite than in FIG. 4) or in a separate holder. It is also possible to use the relatively thick aluminium layer as the support layer 301 in a structure like that of FIG. 3d or 3h.

If an XRF measurement device only comprises one filter changer or otherwise only single means for supporting a selected filter between the X-ray tube and the sample window, it is possible to use a filter module in which the first and second filter layers are attached to each other and/or to a common support frame along their edges, and to attach said filter module to the filter changer or other means for supporting a selected filter between the X-ray tube and the sample window. A filter changer is not necessary for using the two-layer filter arrangement; at least one of the first and second filter layers can be also fixedly installed in the X-ray measurement device.

Regardless of the basic mechanical approach to supporting the filter layers between the X-ray tube and the sample window it is advantageous if the structure of the holders, support frames or the like is such that it is not possible or not easy to attach the filter layers the other way round, i.e. so that the heavier filtering element would be located between the X-ray tube and the lighter filtering element.

It has been found that using a two-layer filter arrangement in accordance with the present invention may improve the detection limit of cadmium by at least 25% compared to conventional XRF measurement devices.

We claim:

1. A filter arrangement for X-ray radiation, comprising:
   a first filter layer comprising a first filtering element, which has an atomic number, and
   a second filter layer comprising a second filtering element, which has an atomic number that is greater than the atomic number of the first filtering element;
   wherein said first filter layer and said second filter layer are adapted to be supported between an X-ray source and a sample to be subjected to X-ray fluorescence analysis, and said first filter layer is adapted to be supported between said X-ray source and said second filter layer, and wherein said second filtering element is one of the group consisting of rhodium and palladium.

2. A filter arrangement according to claim 1, wherein said first filtering element is nickel.

3. A filter arrangement according to claim 2, wherein the first filter layer is a sheet of nickel having a thickness of essentially 20 micrometers, and the second filter layer is a sheet of rhodium or palladium having a thickness of essentially 3.5 micrometers.

4. A filter arrangement according to claim 1, wherein said first filtering element is copper.

5. A filter arrangement according to claim 4, wherein the first filter layer is a sheet of copper having a thickness of essentially 20 micrometers, and the second filter layer is a sheet of rhodium or palladium having a thickness of essentially 3.5 micrometers.

6. A filter arrangement according to claim 1, wherein the first and second filter layers are attached to each other to constitute a single mechanical entity.

7. A filter arrangement according to claim 1, comprising a support layer made of material essentially transparent to X-rays and adapted to mechanically support at least one of said first filter layer and said second filter layer.

8. An X-ray fluorescence measurement device, comprising:
   an X-ray source,
   a sample window for allowing X-rays from said X-ray source reach a sample to be subjected to X-ray fluorescence analysis, and
   a filter arrangement between said X-ray source and said sample window;
   wherein said filter arrangement comprises a first filter layer comprising a first filtering element, which has an atomic number, and a second filter layer comprising a second filtering element, which has an atomic number that is greater than the atomic number of the first filtering element, and said first filter layer is between said X-ray source and said second filter layer, and said second filtering element is one of the group consisting of rhodium and palladium.

9. An X-ray fluorescence measurement device according to claim 8, wherein:
   said X-ray source is an X-ray tube that has an anode, which comprises tungsten as anode material, and
   said first filtering element is nickel.

10. An X-ray fluorescence measurement device according to claim 9, wherein the first filter layer is a sheet of nickel having a thickness of essentially 20 micrometers, and the second filter layer is a sheet of rhodium or palladium having a thickness of essentially 5 micrometers.

11. An X-ray fluorescence measurement device according to claim 8, wherein:
    said X-ray source is an X-ray tube that has an anode, which comprises at least one of rhenium, platinum or gold as anode material, and
    said first filtering element is copper.

12. An X-ray fluorescence measurement device according to claim 11, wherein the first filter layer is a sheet of copper having a thickness of essentially 20 micrometers, and the second filter layer is a sheet of rhodium or palladium having a thickness of essentially 5 micrometers.

13. An X-ray fluorescence measurement device according to claim 8, comprising a filter changer adapted to controllably move at least one filter layer of said filter arrangement into and out of the path between said X-ray source and said sample window.

14. An X-ray fluorescence measurement device according to claim 8, comprising a third filter layer between said first filter layer and said sample window, said third filter layer comprising a third filtering element, which has an atomic number that is smaller than the atomic numbers of the first and second filtering elements.

15. An X-ray fluorescence measurement device according to claim 14, wherein said third filtering layer is a sheet of aluminum having a thickness of essentially 200 micrometers.

* * * * *